(12) United States Patent (10) Patent No.: US 7,811,301 B2
Lebet (45) Date of Patent: Oct. 12, 2010

(54) DEVICE FOR AIDING THE PERCUTANEOUS POSITIONING OF A GUIDING TUBE FOR A NEPHROSCOPE IN KIDNEY SURGERY

(75) Inventor: Alain Lebet, Lausanne (CH)

(73) Assignee: LMA Urology Limited, Victoria, Mahe (SC)

( * ) Notice: Subject to any disclaimer, the term of this patent is extended or adjusted under 35 U.S.C. 154(b) by 1080 days.

(21) Appl. No.: 10/566,479

(22) PCT Filed: Jul. 28, 2004

(86) PCT No.: PCT/FR2004/002013

§ 371 (c)(1),
(2), (4) Date: Apr. 4, 2006

(87) PCT Pub. No.: WO2005/014096

PCT Pub. Date: Feb. 17, 2005

(65) Prior Publication Data

US 2006/0247669 A1 Nov. 2, 2006

(30) Foreign Application Priority Data

Aug. 1, 2003 (FR) .................................. 03 09481

(51) Int. Cl.
*A61B 17/32* (2006.01)
(52) U.S. Cl. ....................................... 606/170; 606/192
(58) Field of Classification Search ................. 606/159, 606/190–192, 194, 195, 197, 167, 170; 604/104.01, 604/167.01, 170.01–170.03, 509, 22, 914, 604/910, 101.04, 164.01; 600/116
See application file for complete search history.

(56) References Cited

U.S. PATENT DOCUMENTS

| 4,273,128 | A | * | 6/1981 | Lary | 606/159 |
| 4,583,974 | A | * | 4/1986 | Kokernak | 604/211 |
| 4,654,027 | A | * | 3/1987 | Dragan et al. | 604/99.03 |
| 5,009,659 | A | * | 4/1991 | Hamlin et al. | 606/159 |
| 5,304,121 | A | * | 4/1994 | Sahatjian | 604/509 |
| 5,336,234 | A | * | 8/1994 | Vigil et al. | 606/159 |
| 5,707,382 | A | | 1/1998 | Sierocuk et al. | |
| 5,810,790 | A | | 9/1998 | Ebling et al. | |
| 6,475,185 | B1 | * | 11/2002 | Rauker et al. | 604/96.01 |

FOREIGN PATENT DOCUMENTS

DE 3206381 A 9/1983

* cited by examiner

*Primary Examiner*—Todd E Manahan
*Assistant Examiner*—Christopher Schubert
(74) *Attorney, Agent, or Firm*—Ostrager Chong Flaherty & Broitman P.C.

(57) ABSTRACT

The invention relates to a device for positioning a guiding tube (1) for a nephroscope, said tube consisting of a long aspiration needle (2) which is provided with a closing mandrin (3) and on which an inflatable enlargement device (4) slides, said device especially comprising a cuff (25) which is positioned by sliding along the aspiration needle (2) that is previously inserted into the kidney of the patient. The operation is facilitated by a trocar consisting of cutting blades (19) which enlarge the opening without tearing any flesh. The cuff is then inflated so that the inflatable enlargement device (4) can be used as a guiding means for a guiding tube for a nephroscope during the positioning thereof in the kidney of the patient.

20 Claims, 2 Drawing Sheets

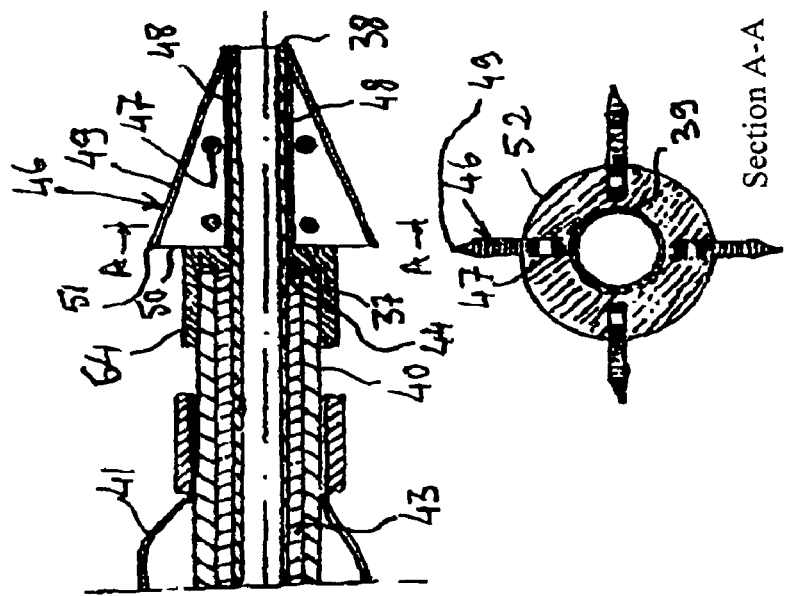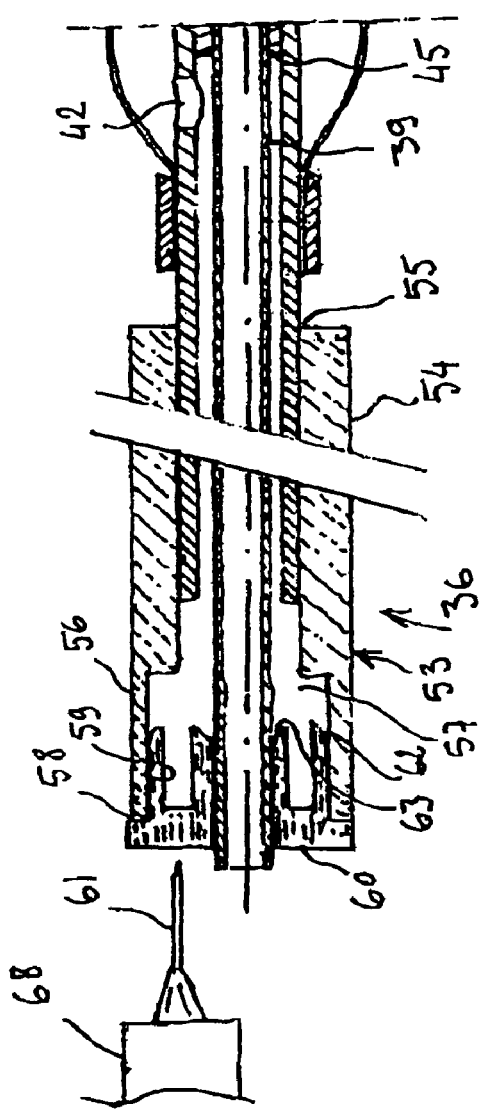

DEVICE FOR AIDING THE PERCUTANEOUS POSITIONING OF A GUIDING TUBE FOR A NEPHROSCOPE IN KIDNEY SURGERY

The invention relates to a device for aiding the percutaneous positioning of a guiding tube for a nephroscope in kidney surgery. The guiding tube to be positioned is in a plastic material cover, semi-translucent under X-ray, to the order of ten millimeters in diameter featuring a shoulder on the outer end side; the positioning of such a guiding tube, also referred to as "sheat" is currently performed according to various methods: this firstly consists of inserting an aspiration needle of a diameter of thirteen to twenty gauges from the surface of the skin into the kidney; this aspiration needle is a hollow needle closed, through its entire length, by a mandrin during the aspiration needle pushing phase into the kidney, when the penetration depth allows the renal pelvis to be reached, the mandrin is removed in order to verify that a urine outflow occurs, indicating that the aspiration needle end is effectively in the renal pelvis; on the one hand, a flexible metallic guide is then engaged into the aspiration needle, which is then removed, and, on the other, a first expander tube, called "Alken expander tube", is engaged onto the metallic tube by sliding, until its distal end abuts on the end of the flexible metallic guide which has coiled up; the inner diameter of the first expander tube is to the order of thirteen to twenty gauges, and its thickness to the order of one third of a millimeter, that is to say a "free unit" or "franche" (which is a unit of measure used in surgical technologies); the first expander tube features a shoulder at its distal end, which acts as an arrester for a series of multi-stage expander tubes which slide one above the other in order to increase the diameter of the opening cut in the kidney; each one of the Alken expander tubes increases the diameter of the opening by two "free units" or "franches" and, when its diameter is sufficient, the guiding tube can be slid onto the last expander tube; then, the set of expander tubes only has to be removed; this process requires a large number of X-ray short checks.

Another, quicker method consists of sliding onto the needle a metallic support tube comprising an inflatable cuff; the cuff is comprised of a flexible envelope surrounding the support tube and featuring moderate elasticity; when inflated, the envelope is of long-shaped cylindrical revolution form in its central section, going smaller at its ends until reaching a diameter practically equal to the support tube diameter, the ends of the cuff are then crimped onto the support tubes by means of metallic crimping tubes; the envelope which makes up the cuff comprises an inflation pipe which allows the introduction of the necessary and sufficient volume of inflation fluid so that the central section will reach a diameter practically equal to that of the guiding tube to be positioned; before the kidney opening enlargement operation by introduction and inflation of the cuff, it is necessary to perform radial cuts in the patient's flesh, by means of a bistoury around the needle in order to avoid tearing the flesh at the time of inflation (which would make healing more difficult); when the inflation diameter is reached, it is only necessary to slide the guiding tube onto the cuff envelope which is lubricated by an impregnation coating at cuff surface and which simply obtains its lubrication function by simple humidification; then, when the guiding tube is positioned, the assembly comprising the support tube and the aspiration needle is removed. The opening enlargement operation is difficult to perform manually, especially in depth, and as, for the most part, no visual monitoring is possible: this does not guarantee the avoidance of flesh tearing around the opening.

On the other hand, there are flexible metallic guides which are engaged into the aspiration needle and remain in place when the aspiration needle is removed so that they can be used in case of a problem during the operation; a flexible metallic guide is comprised of a cylindrical mechanic core surrounded by a plastic thread coiled in solid coils (coils touching); form memory metals*** are available: in wire form, they feature an initial shape which can be freely changed, but they return to their initial shape as soon as certain conditions are met.

The object of the invention consists of a guiding tube positioning device, usable once, for rapidly positioning a nephroscope guiding tube.

The description below is based upon the following illustrations:

FIG. 2 is a longitudinal cross-sectional view of a guiding tube positioning device in accordance with the invention, assembled by plastic material overmoulding.

FIG. 3 is a cross-sectional view of the trocar assembly in accordance with FIG. 2.

Figure 1:
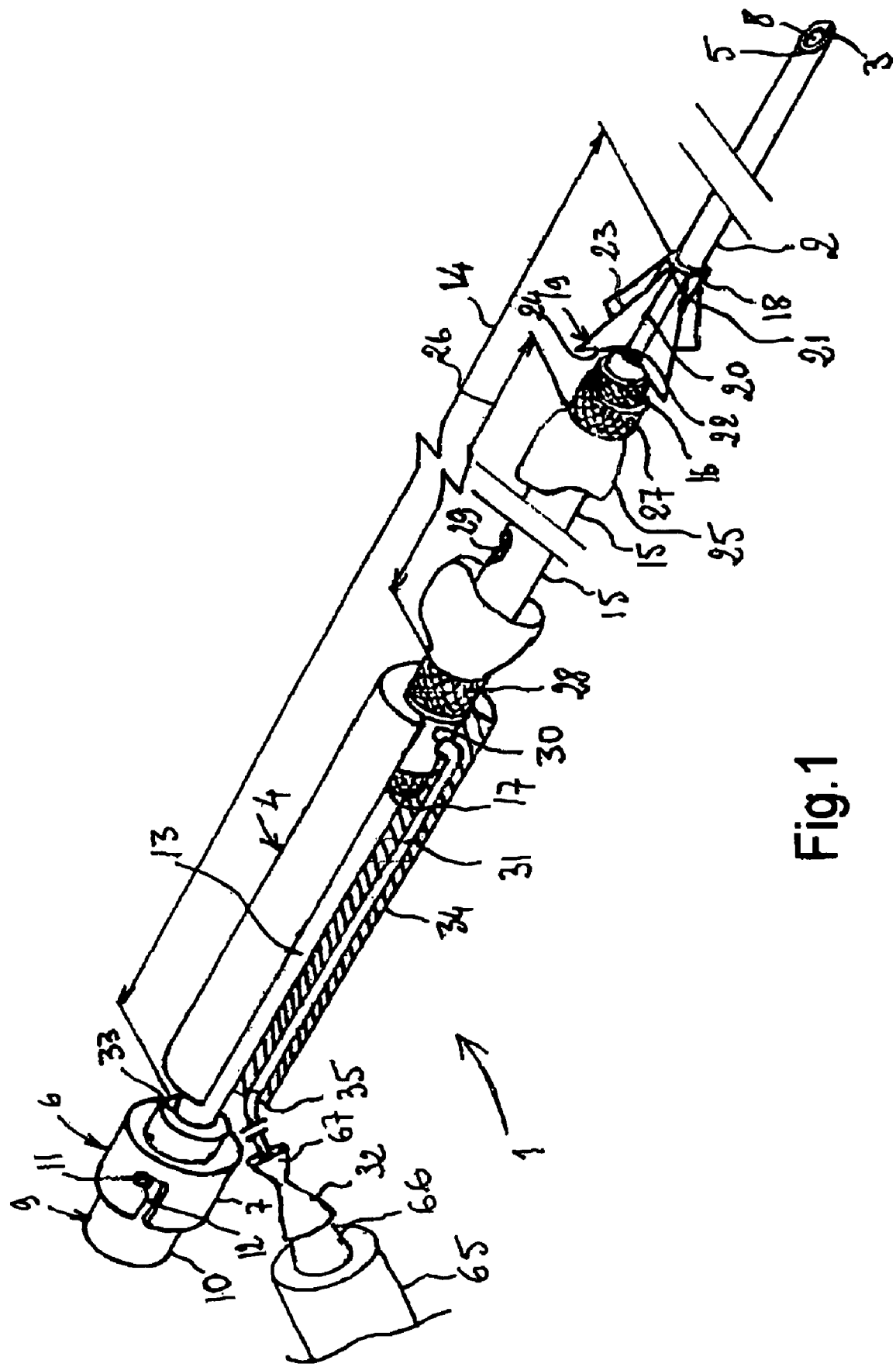
FIG. 1 is a perspective exploded view of a guiding tube positioning device in accordance with the invention.

The invention consists of a nephroscope positioning guiding tube positioning device 1 (FIG. 1), comprised of a long aspiration needle 2 fitted with a closing mandrin 3, on which an inflatable enlargement device 4 slides, said enlargement device being shorter than the aspiration needle 2 which serves as its guiding means, whereas inflatable enlargement device 4 serves as guiding means for a nephroscope guiding tube at the time of its positioning on a patient. Aspiration needle 2 features a first needle end 5 cut skewed and a second needle end 6 comprising a needle sleeve 7 which surrounds the lateral section of the second needle end, practically cylindrical in revolution and preferably coaxial to the aspiration needle 2, featuring a diameter appreciably inferior to that of the guiding tube to be positioned; the length of the aspiration needle is practically double the length necessary to reach the renal pelvis so that one half of position needle 2, located on the same side as second needle end 6, serves as support for inflatable enlargement device 4 during the operation phase consisting of introducing first needle end 5 into the renal pelvis. Aspiration needle 2 comprises a closing mandrin 3 whose first mandrin end 8 is cut skewed like first end 5 of aspiration needle 2, and located in the same plane as that of first needle end 5, whereas second mandrin end 9 comprises a securing and directing device 10 for closing mandrin 3 onto needle sleeve 6; securing and directing device 10 is comprised, for example, of securing system 12 in which at least one stud 11 solid with second mandrin end 9 is clamped: when closing mandrin 3 is removed, it is replaced by a form memory guide (not illustrated) which is normally curved at its end but which can be initially kept straight, for example, by mechanical deformation for the time necessary to pass through aspiration needle 2 and into the kidney; as soon as the form memory guide end protrudes, at first needle end 5, it reassumes its form and thereby acts as a positioning arrester for inflatable enlargement device 4; closing mandrin 3 can advantageously supersede the positioning of a guide by creating said guide by means of a form memory metal and by using needle sleeve 7, in two sections, a part of which is used as an arrester for second mandrin end 9) and is removable, and allows first mandrin end 8 to protrude from first needle end 5, thereby assuming the shape of an arrester elbow.

Inflatable enlargement device 4 is comprised of a sliding tube 13, which is metallic, whose inner diameter is slightly larger than that of aspiration needle 2, and whose length 14 is preferably less than one half of the length of aspiration needle 2; said sliding tube 13 is likely to slide along the entire aspiration needle 2 and to escape therefrom by first needle end 5; a support tube 15, shorter than sliding tube 13, surrounds sliding tube 13 to which it is attached by its ends 16 and 17 in a sealed manner; the inner diameter of support tube 15 is larger than the outer diameter of sliding tube 13, of the necessary and sufficient value to allow a pressurised inflation fluid to flow; sealing between sliding tube 13 and support tube 15 is obtained, for example, by shrinkage or by hitting a centring sleeve (not illustrated) between sliding tube 13 and support tube 15 followed, for example, by a sealing process by introduction of solder by capillarity between sliding tube 13 and support tube 15, on the one hand, and the centring sleeve on the other; sliding tube 13 features a first sliding tube end 18 directed towards first needle end 5, which comprises at least two cutting blades 19, essentially shaped into a right-angled triangle placed in a symmetry plane passing by the centreline of sliding tube 13 and, for example, symmetrical to each other with respect to said centreline; a first blade side 20 of each one of the triangles constituting cutting blades 19 is slid with sliding tube 13, to which it is attached following a generatrix of sliding tube 13; a manner for securing cutting blades 19 consists of welding them to sliding tube 13, for example, by means of laser welding; a first end of first blade side 21 practically coincides with the first end of sliding tube 18, located on the same side as first needle end 5; a second end of first blade end 22 is located immediately adjacent to a first end of support tube 16; a second blade side 23 of each cutting blade 19 comprises a cutting thread; a first end of second blade side is the same as the first end of first blade side 21; first blade side 20, forming an angle to the order of five to ten degrees with second blade side 23; second blade side 23 is preferably profiled to allow better efficiency of the cut performed by the cutting thread, for example, by shaping it into a concave form; a third blade side 24, which is not cutting, is practically perpendicular to first blade side 20 and features a length such that the cumulation of the diameter of sliding tube 13 and of the length of both symmetrical third blade sides 24 corresponds to the order of magnitude of the inner diameter of the guiding tube to be positioned. In a preferred embodiment of the invention, there are four to six cutting blades 19; when, for example, four blades are used, they are symmetrical to each other by twos, following to symmetry planes, perpendicular to each other, and passing by the symmetry axis of sliding tube 13: the angle between second and third sides 23 and 24 of blade is replaced by a rounded shape; said set of cutting blades 19 is referred to as "a trocar". A cuff 25, of a length 26 practically equal to that of the cuffs already used, covers support tube 15 on which it is secured, at its ends 27 and 28, for example, by crimping tubes as previously described: a first cuff end 27 is immediately adjacent to third blade sides 24 and to first support tube end 16; second cuff end 28 is secured to support tube 15, which is appreciably longer than cuff 25; a first orifice 29, on the one hand, is opened in support tube 13, in the area located inside cuff 25 and, a second orifice 30, on the other hand, is also open in said support tube and said second end is external to cut 25; second orifice 30 is connected to a filling tube 21, fitted with a closing device 67, likely to communicate with pressurised inflation fluid supply device 65, for example, via a connection device comprised of first connection interface device 32, solid with filling tube 31, and second connection interface device 66, solid with pressurised inflation fluid supply device 65; a pressurised inflation fluid supply device 65 is, for example, a syringe comprised of a cylindrical chamber in which a piston slides, and said piston's control rod is threaded and screwed into a nut which is solid with the clamber; by counting the number of turns of the control rod in the screwing direction, it is possible to accurately determine the inflation fluid volume delivered by supply device 65; second connection interface device 66 is comprised, for example, of a male cone which engages into a female cone constituting first connection interface device 32; the inflation fluid is, for example, physiological saline solution; closing device 67 is, for example, a ball-type device whose ball is pressed onto a taper seat by a spring, and which allows the inflation fluid to flow from supply device 65 to flow into cuff 25, but which prevents the inflation fluid from returning; the outer surface of cuff 25 is coated with a substance which becomes sticky at water contact and which allows lubrication to be ensured for guide tube sliding onto the cuff; the filling tube can be metallic and welded to support tube 15 at second orifice 30; to permit guiding tube passage, the assembly comprised of support tube 15, sliding tube 13, filling tube 31 fitted with its first connection interface device 32, must hold within a virtual revolution cylindrical volume whose symmetry axis is that of sliding tube 13, and whose diameter is inferior to the inner diameter of the guiding tube; finally, the part of sliding tube 13 located next to second sliding tube end 33, and as required, the part of support tube 15 and of filling tube 31, located next to second support tube end 17, are covered with a handling sleeve 34, holding within the above-defined virtual revolution cylindrical volume, whose second end, located next to second sliding tube end 33, is positioned with respect to the latter, so that sliding tube 13 will not hinder connection of supply device 65.

A method for industrialising manufacturing of a device for aiding positioning of guiding tube 36 (FIG. 2), consists, for example, of using plastic material to jointly assemble the main components of the device for aiding positioning of guiding tube 36, by the overmoulding method.

A first overmoulding concerns the zone located on the side of first ends 37 and 38 of sliding tube 39 and of support tube 40; support tube 40 comprises, at the time of its implementation, cuff 41 which communicates with the inside of support tube 40 through first orifice 42; support tube 40 is positioned with respect to sliding tube 29, by means of centring sleeve 43 whose first centring sleeve end 44 begins, for example, at the first end of support tube 37, and whose length is such that the second of centring tube 45 will not close first orifice 42; the assembly comprised of sliding tube 39, support tube 40 and centring sleeve 43 is introduced through the first end of sliding tube 38 into a suitable first end recess (not illustrated) of an injection mould:

said first end recess includes, notably, a core to be introduced and adjusted inside the sliding tube in order to avoid material penetration; cutting blades 46, which comprise blade holes 47 along first blade side 48, are each positioned in a housing of the injection mould (not illustrated) which protects second blade side 49, which is the cutting part, as well as the part of third blade side 50 located on the same side as the second end of second blade side 51; when the thermoplastic material is injected, it forms, for example, a sort of truncated revolution section 52 (FIG. 3) encasing the base of cutting base 46 which are locked by the plastic material passing through blade holes 47; the truncated revolution section 52 encasing sliding tube 39; the truncated revolution section 52 protruding beyond third blade sides 50 (FIG. 2) by a sealing 64 which covers the first end of support tube 37 over a sufficient length to ensure tightness to the fluids in the space located between sliding tube 39 and support tube 40, and without disturbing cuff 41.

A second overmoulding allows the manufacturing of handling 53 (FIG. 2) whose first solid sleeve part 54 is located on the same side as first sleeve end 55, and directed towards cuff (41), covering a zone of support tube (40), whereas a second sleeve part 56, which being hollowed in order to constitute filling tube 57; second sleeve end 58 being comprised of a sleeve neck 59, open to the outside, and through which sliding tube 39 passes, coaxially.

Although the pressure required for inflation of cuff 41 can be relatively high, the residual pressure after inflation is much lower, and consequently, a first connecting and closing interface device can be constituted with a simple rubber plug 60 which is inserted into the sleeve neck 59 in order to close filling tube 57 and, at the same time, making up the first connection interface device whereas the second interface device is comprised of a needle 61, for example, for hypodermic injections, which allows piercing through rubber plug 60 in order to inject the inflation fluid contained in supply device 68 and comprised, for example, of a syringe; rubber plug 60 keeps a sufficient sealing function when needle 61 is removed.

More particularly, it is then possible to close sleeve neck 59 by means of rubber plug 60 featuring an external sealing skirt 62 and an internal sealing skirt 63; external sealing skirt 62 ensures sealing of the internal side of sleeve neck 59 and internal sealing skirt 63 ensures sealing with the external side of sliding tube 39.

Initially, aspiration needle 2 (FIG. 1) equipped with its mandrin 2 is; in place in inflatable enlargement device 4 with its needle sleeve 7 abutting on second sliding tube end 33 of sliding tube 13; by resting against needle sleeve 7, aspiration needle 2 is firstly inserted into the kidney through the patient's skin, until its end reaches the renal pelvis; the closing mandrin 3 is then removed, in order to note the urine outflow from aspiration needle 2 and either closing mandrin 3 is then put back in place after removing the removable part of needle sleeve 7 (which serves as arrester for second mandrin end 9), or a form memory guide is put in place; inflatable enlargement device 4 is then inserted by sliding along aspiration needle (2) which is used as a guide; inflatable enlargement device 4 is inserted into the kidney by resting on handling sleeve 34 until first sliding tube end 18 reaches first aspiration needle end 5 located in the renal pelvis and materialised by the curved end of closing mandrin 3, or of the form memory guide; aspiration needle 2 can then be removed in case of use of a form memory guide; however, it must remain in place in case of use of a form memory closing mandrin; supply device 65 is connected onto filling tube 31 and cuff 25 is inflated in a controlled manner; then, the guiding tube is put in place and the inflatable enlargement device is removed whereas, as required, the form memory guide can be kept in place and, in case of use of a form memory closing mandrin, by placing at least one guide as replacement for inflatable enlargement device 4.

The invention claimed is:

1. A device for positioning a guiding tube (1) for a nephroscope, comprising:
    an aspiration needle (2) having a first distal end and a second distal end; and
    an inflatable enlargement device (4, 36) slidably positioned around the aspiration needle between the first and second distal ends such that the aspiration needle serves as a guide means for the inflatable enlargement device (4, 36), the inflatable enlargement device serving as the guide tube for the nephroscope at the time of its positioning on a patient; the inflatable enlargement device comprising:
        a sliding tube (13, 39) positioned around the aspiration needle such that it slides along the aspiration needle and having a first sliding tube end (18) comprising at least two cutting blades (19, 46) making up a trocar and a second sliding tube end (33) comprising a handling sleeve (34, 53);
        a support tube (15, 40) shorter in length than the sliding tube, positioned around the sliding tube and attached at its ends to the sliding tube, a first support tube end positioned adjacent to the cutting blades, and
        a cuff (25, 41) surrounding the support tube (15, 40) and secured to the support tube at a first cuff end and a second cuff end, the first cuff end positioned immediately adjacent the first support tube end;
        the support tube having an inner diameter that is larger than an outer diameter of the sliding tube to form an inflation fluid circulation space where a pressurized inflation fluid can flow between the sliding tube and the support tube,
        the inflation fluid circulation space communicating with an inside area of the cuff through a first orifice (29, 42) opened in the support tube inside the cuff (25, 41) and with a filling tube (31, 57) through a second orifice opened in the support tube outside the cuff, such that an interior area of the cuff is in fluid communication with a supply of pressurized inflation fluid connected to the filling tube.

2. A device according to claim 1, further comprising a closing mandrin (3) removably fitted within an interior of the needle and extending from the first distal end to the second distal end, the second distal end fitted with a needle sleeve (7) surrounding an exterior surface of the second distal end and having a diameter appreciably inferior to a diameter of the guiding tube (1), the closing mandrin having means for securing the closing mandrin to the needle sleeve (7).

3. A device according to claim 2, wherein the needle sleeve (7) comprises a removable part whose removal permits inserting the closing mandrin further into the needle sleeve and thereby forming an arrester elbow.

4. A device according to claim 2, wherein the closing mandrin comprises a form memory metal, and the closing mandrin has an end that protrudes from the first distal end of the aspiration needle to form an arrester elbow.

5. A device according to claim 1, wherein the supply of pressurized inflation fluid comprises an inflation fluid supply device (65, 68) containing the inflation fluid a connection means for connecting the inflation fluid supply device to the filling tube such that the inflation fluid is permitted to flow from the supply device into the cuff, but prevented from returning to the inflation fluid supply device.

6. A device according to claim 5, wherein the connection means comprises a closing device (67) comprised of a ball-type device whose ball is pressed against a tapered seat by a spring, and which allows the inflation fluid of supply device (65) to flow towards the cuff (25), but which prevents said inflation fluid from flowing back.

7. A device according to claim 6, wherein the connection means further comprises a second connection interface (66) comprised of a male cone which engages into a female cone of a first connection interface device (32).

8. A device according to claim 6, wherein the connection means further comprises a first connection interface device comprised of a rubber plug (60) cooperating with a second connection interface device comprised of a needle (61).

9. A device according to claim 6, wherein the supply device (65, 68) is comprised of a syringe having a cylindrical chamber in which a piston slides, and a control rod threaded and screwed into a nut at an end of the chamber.

10. A device according to claim 1, wherein the support tube (15, 40) is connected by at least one of its ends (16, 17, 44) to the sliding tube (13, 39) in a sealed manner.

11. A device according to claim 10, wherein a centring plug (43) is positioned between the sliding tube (13) and the support (15) to form a sealed connection between the support tube and the sliding tube.

12. A device according to claim 11, wherein the sealed connection further comprises a weld by capillarity between the sliding tube, the support tube and the centring plug.

13. A device according to claim 11, wherein the sealed connection further comprises a sealing cylinder (64) made of plastic material.

14. A device according to claim 1, wherein the at least two cutting blades having a triangular shape with a first blade side (20, 48) secured to the sliding tube (13, 39) along one of its generatrices, a second blade side (23, 49) having a cutting thread forming an angle with the first blade side (20), and a top edge substantially coincident with the first sliding tube end (18) to the order of five to ten degrees.

15. A device according to claim 1, wherein the at least two cutting blades comprise four to six cutting blades.

16. A device according to claim 1, wherein a connection between the cutting blades (19) and the sliding tube (13) comprises a laser weld.

17. A device according to claim 1, wherein each of the at least two cutting blades has a first blade side (20, 48), a base, and blade holes (47) along the first blade side (48), the base of the cutting blades being encased in a truncated revolution cone (52), made of plastic material, such that the sliding tube is encased and the cutting blades (46) are locked with respect to the sliding tube (39) by the plastic material passing through the blade holes (47).

18. A device according to claim 1, wherein the an outer surface of the cuff (25, 41) is coated with a substance which becomes sticky at water contact in order to lubricate the guide tube (1, 36) for sliding along said cuff.

19. A device for positioning a guiding tube (1) for a nephroscope on a patient, comprising:
an aspiration needle (2) having a first distal end and a second distal end, and a closing mandrin (3) removably fitted within an interior of the needle and extending from the first distal end to the second distal end, the second distal end fitted with a needle sleeve (7) surrounding an exterior surface of the second distal end and having a diameter appreciably inferior to a diameter of the guiding tube (1), the closing mandrin having means for securing the closing mandrin to the needle sleeve (7), the closing mandrin comprising a form memory metal, and having an end that protrudes from the first distal end of the aspiration needle to form an arrester elbow; and
an inflatable enlargement device (4, 36) slidably positioned around the aspiration needle between the first and second distal ends such that the aspiration needle serves as a guide means for the inflatable enlargement device (4, 36), the inflatable enlargement device serving as the guide tube for the nephroscope at the time of its positioning on a patient; the inflatable enlargement device comprising:
a sliding tube (13, 39) positioned around the aspiration needle such that it slides along the aspiration needle and having a first sliding tube end (18) comprising at least two cutting blades (19, 46) making up a trocar and a second sliding tube end (33) comprising a handling sleeve (34, 53);
a support tube (15, 40) shorter in length than the sliding tube, positioned around the sliding tube and attached at its ends to the sliding tube, a first support tube end positioned adjacent to the cutting blades, and
a cuff (25, 41) surrounding the support tube (15, 40) and secured to the support tube at a first cuff end and a second cuff end, the first cuff end positioned immediately adjacent the first support tube end;
the support tube having an inner diameter that is larger than an outer diameter of the sliding tube to form an inflation fluid circulation space where a pressurized inflation fluid can flow between the sliding tube and the support tube,
the inflation fluid circulation space communicating with an inside area of the cuff through a first orifice (29, 42) opened in the support tube inside the cuff (25, 41) and with a filling tube (31, 57) through a second orifice opened in the support tube outside the cuff, such that an interior area of the cuff is in fluid communication with a supply of pressurized inflation fluid connected to the filling tube, the supply of pressurized inflation fluid comprising an inflation fluid supply device (65, 68) containing the inflation fluid and connection means for connecting the inflation fluid supply device to the filling tube such that the inflation fluid is permitted to flow from the supply device into the cuff, but prevented from returning to the inflation fluid supply device.

20. A device according to claim 19, wherein the an outer surface of the cuff (25, 41) is coated with a substance which becomes sticky at water contact in order to lubricate the guide tube (1, 36) for sliding along said cuff.

* * * * *

UNITED STATES PATENT AND TRADEMARK OFFICE
CERTIFICATE OF CORRECTION

| | | |
|---|---|---|
| PATENT NO. | : 7,811,301 B2 | Page 1 of 1 |
| APPLICATION NO. | : 10/566479 | |
| DATED | : October 12, 2010 | |
| INVENTOR(S) | : Alain Lebet | |

It is certified that error appears in the above-identified patent and that said Letters Patent is hereby corrected as shown below:

Col. 6, line 44, change "fluid a connection" to --fluid and connection--.

Signed and Sealed this
Eighteenth Day of January, 2011

David J. Kappos
*Director of the United States Patent and Trademark Office*